United States Patent
Thiel et al.

(10) Patent No.: US 10,584,957 B2
(45) Date of Patent: Mar. 10, 2020

(54) TERAHERTZ MEASUREMENT METHOD AND TERAHERTZ MEASURING APPARATUS FOR ASCERTAINING A LAYER THICKNESS OR A DISTANCE OF A MEASUREMENT OBJECT

(71) Applicant: INOEX GmbH Innovationen und Ausruestungen fuer die Extrusionstechnik, Melle (DE)

(72) Inventors: Marius Thiel, Osnabrueck (DE); Ralph Klose, Melle (DE)

(73) Assignee: INOEX GmbH Innovationen und Ausruestungen fuer die Extrusionstechnik, Melle (DE)

( * ) Notice: Subject to any disclaimer, the term of this patent is extended or adjusted under 35 U.S.C. 154(b) by 11 days.

(21) Appl. No.: 16/062,662

(22) PCT Filed: Dec. 12, 2016

(86) PCT No.: PCT/DE2016/100577
§ 371 (c)(1),
(2) Date: Jun. 15, 2018

(87) PCT Pub. No.: WO2017/101906
PCT Pub. Date: Jun. 22, 2017

(65) Prior Publication Data
US 2018/0347963 A1     Dec. 6, 2018

(30) Foreign Application Priority Data
Dec. 18, 2015   (DE) .................... 10 2015 122 205

(51) Int. Cl.
*G01B 11/245*  (2006.01)
*G01B 11/02*   (2006.01)
(Continued)

(52) U.S. Cl.
CPC ........ *G01B 11/026* (2013.01); *G01B 11/0691* (2013.01); *G01B 11/245* (2013.01); *G01N 21/3586* (2013.01)

(58) Field of Classification Search
CPC ........... G01B 11/0633; G01B 11/0691; G01N 21/03; G01N 21/55
See application file for complete search history.

(56) References Cited

U.S. PATENT DOCUMENTS 9,354,168 B2   5/2016   Sartorius et al.
9,791,263 B2   10/2017  Hochrein
(Continued)

FOREIGN PATENT DOCUMENTS

DE   10 2011 112 697 A1   2/2013
DE   10 2013 217038 A1    3/2015
(Continued)

OTHER PUBLICATIONS

German Office Action in DE 10 2015 122 205.1, dated Oct. 5, 2016, with English translation of relevant parts.
(Continued)

*Primary Examiner* — Hung Nguyen
(74) *Attorney, Agent, or Firm* — Collard & Roe, P.C.

(57) ABSTRACT

The invention relates to a method and a terahertz measuring apparatus for measuring a layer thickness and/or a distance, wherein at least one terahertz beam (7a) is radiated from a terahertz transmission and reception unit (4) along an optical axis (C) onto the measurement object (2, 102) and terahertz radiation (7) that has passed through at least one layer (3) of the measurement object (2, 102) and having been reflected is detected wherein a measurement signal (A) of the detected reflected terahertz radiation (7b) is evaluated and a layer thickness (d) is ascertained from a propagation time difference (t2–t1) of the radiation (7) reflected at boundary layers (2a, 2b) of the layer (3).

(Continued)

Figure 1:
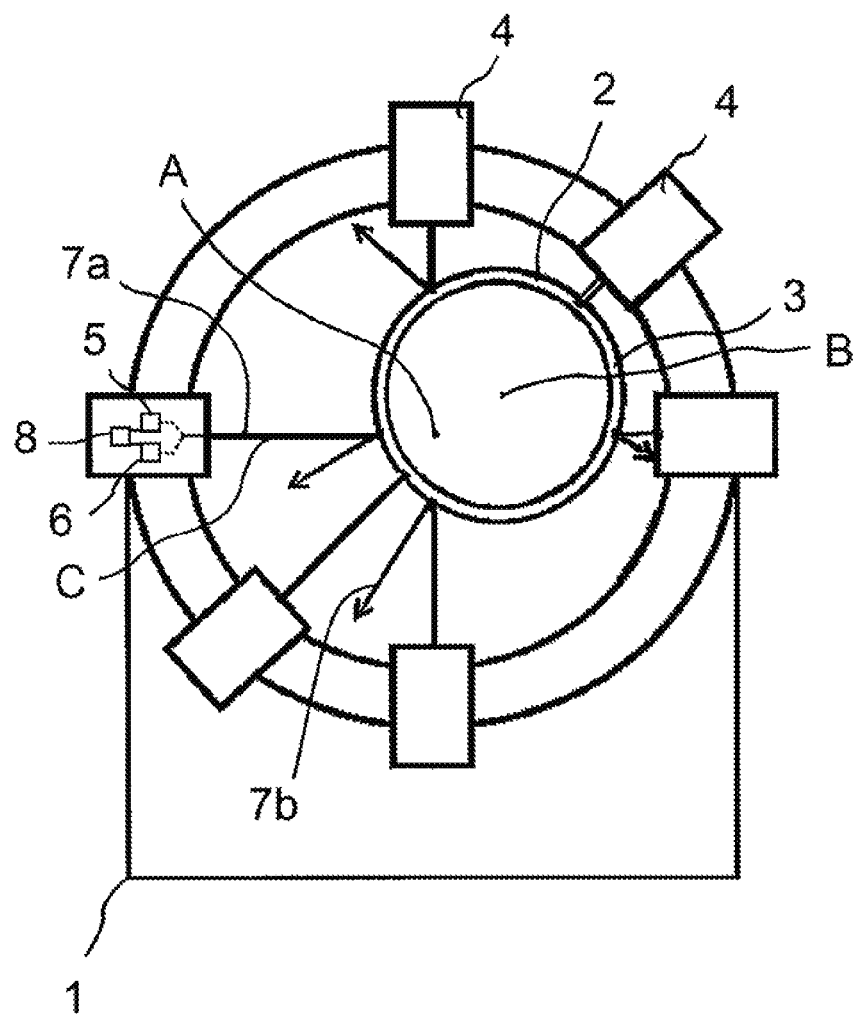

In this case, there is a provision for multiple measurements to be performed using different optical axes (C), wherein the optical axis (C) of the emitted terahertz radiation (7a) is adjusted during the measurements or between the measurements and one of the multiple measurements is used for ascertaining the layer thickness (d).

Preferably, the optical axis is adjusted continuously and/or periodically within an adjustment angle range ($\alpha$) and in the process the multiple measurements are recorded, the measurement therefrom with maximum amplitude being used as the measurement for ascertaining the layer thickness.

14 Claims, 5 Drawing Sheets

(51) Int. Cl.
  G01B 11/06 (2006.01)
  G01N 21/3586 (2014.01)

(56) References Cited

U.S. PATENT DOCUMENTS

| | | | |
|---|---|---|---|
| 2005/0087690 A1* | 4/2005 | Usami | G01N 21/03 250/341.1 |
| 2010/0195090 A1* | 8/2010 | Ohtake | G01B 11/0625 356/51 |
| 2017/0023354 A1 | 1/2017 | Stich | |

FOREIGN PATENT DOCUMENTS

| | | |
|---|---|---|
| DE | 10 2013 223945 A1 | 5/2015 |
| DE | 10 2014 214046 B3 | 10/2015 |

OTHER PUBLICATIONS

J. Hauck et al: "Terahertz Inline Wall Thickness Monitoring System for Plastic Pipe Extrusion", AIP Conference Proceedings, 1593, pp. 86-89, Jan. 1, 2014.

International Search Report of PCT/DE2016/100577, dated Mar. 16, 2017.

* cited by examiner

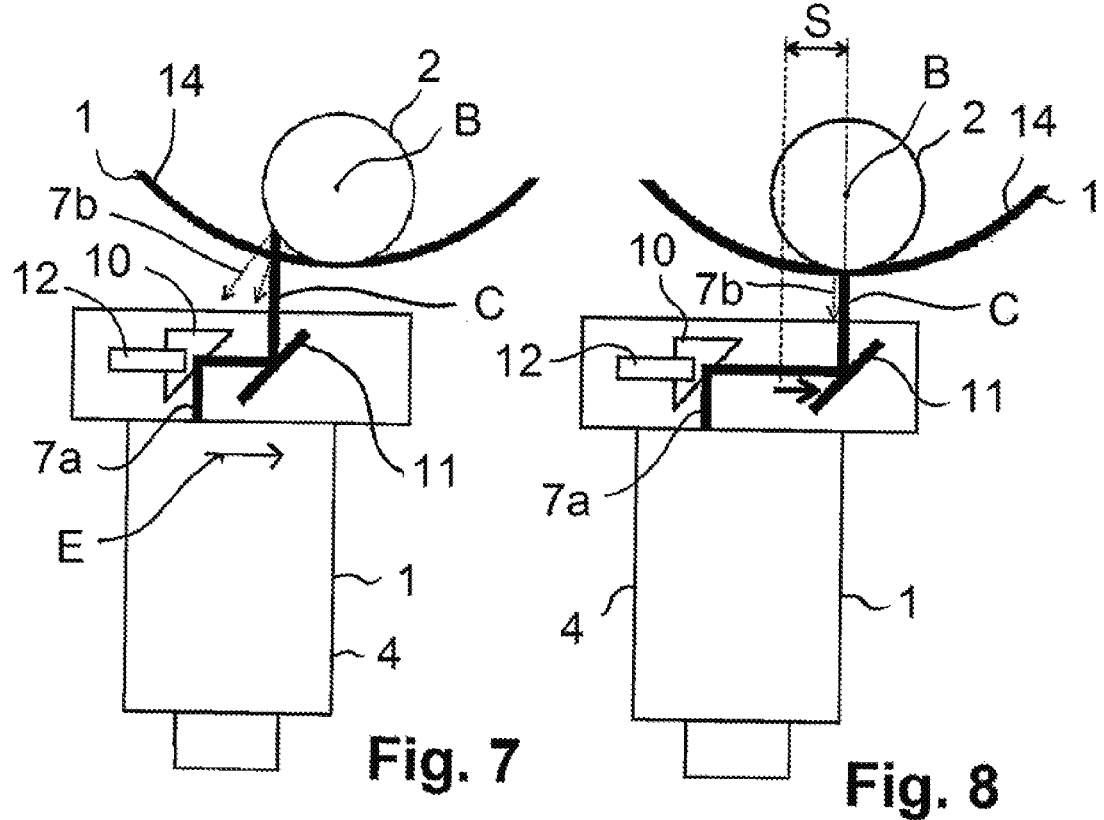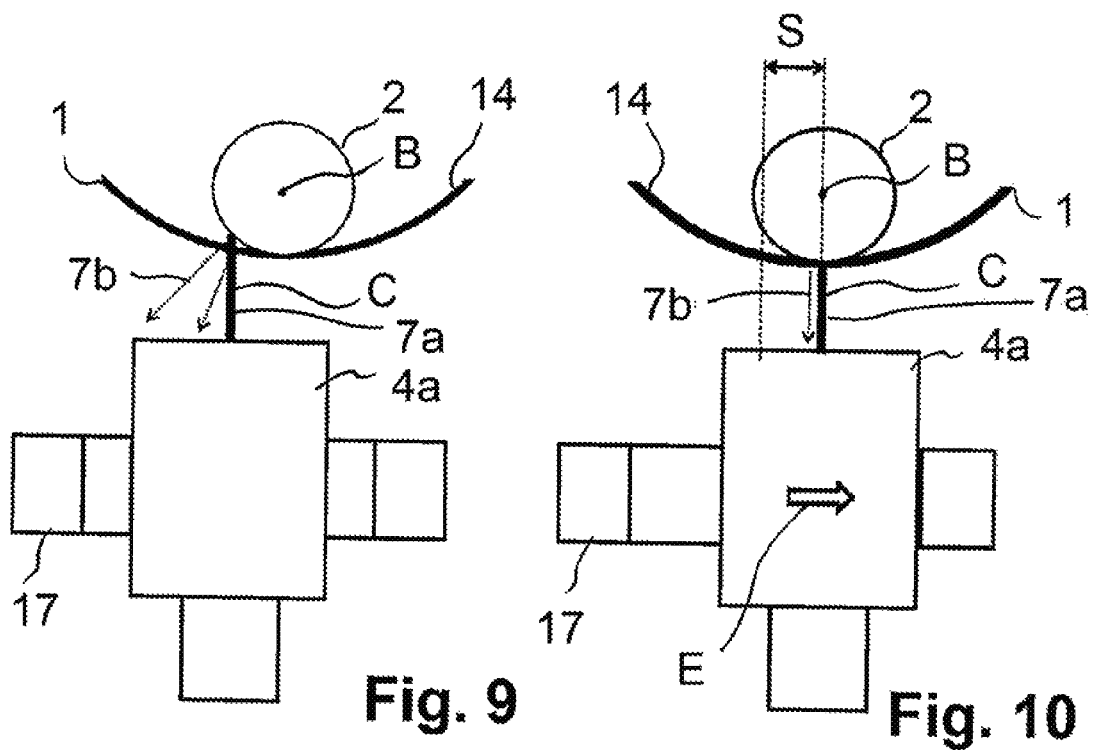

TERAHERTZ MEASUREMENT METHOD AND TERAHERTZ MEASURING APPARATUS FOR ASCERTAINING A LAYER THICKNESS OR A DISTANCE OF A MEASUREMENT OBJECT

CROSS REFERENCE TO RELATED APPLICATIONS

This application is the National Stage of PCT/DE2016/100577 filed on Dec. 12, 2016, which claims priority under 35 U.S.C. § 119 of German Application No. 10 2015 122 205.1 filed on Dec. 18, 2015, the disclosure of which is incorporated by reference. The international application under PCT article 21(2) was not published in English.

The invention relates to a method and a terahertz measuring apparatus for measuring a layer thickness or a distance of a measurement object.

Hereby, terahertz radiation is radiated along an optical axis onto the measurement object made from a material transparent for THz radiation, e.g. plastics, which has, for the terahertz radiation, a markedly higher refraction index compared to air or vacuum. Such a material may be, in particular, a plastic material, but also e.g. wood, ceramics or a fiber reinforced material such as CFK or GFK (carbon fiber reinforced plastics, glass fiber reinforced plastics). One part of the incident terahertz radiation is reflected upon entering the material layer, and one part of the terahertz radiation having penetrated the material layer is reflected on a subsequent boundary surface, for example a leeward or back side of the material layer upon transiting into air. Thus measurement peaks of the amplitude of the radiation reflected on the boundary layers can be detected and the temporal difference of the two measurement peaks evaluated as run-time of the double transit of the material layer. Hereby, the layer thickness of the material layer at the point under investigation can be determined. Moreover, a distance between the measurement object and the transmitter-receiver unit can be determined so that outside dimensions of the measurement object such as e.g. out outer diameter can be determined also.

Terahertz layer thickness measurements of this type can be carried out, in particular, for checking the quality of a plastics object following the making thereof, e.g. immediately after manufacturing, in that the measurement object at the end of a production line is conveyed by the transport device directly to or through respectively the measuring apparatus.

Hereby it has become apparent, however, that in particular in the case of continued measuring of measurement objects at the end of a production line an exact alignment of the terahertz measuring apparatus in relation to the picture object is not always possible. In the event of an imprecise centering of the measurement object, for example, lack of tube centering of the plastic pipe in the measuring apparatus, the incident terahertz radiation with its optical axis no longer hits the surface of the measurement object perpendicularly so that the radiation reflected on the boundary layers is reflected back to the transmitter-receiver unit no longer along the optical axis and the signal strength or amplitude strength is markedly reduced due to the lateral irradiation.

Thus high efforts for positioning are required, for example, by means of mechanically guiding the measurement object; moreover, an immediate measuring after manufacturing a plastics object, sometimes involving plastic materials still soft, is impossible sometimes.

The invention is based on the object of enabling a secure terahertz measuring of a measurement object and a precise determination of a layer thickness and/or a distance.

This task is solved by a measuring method according to one aspect of the invention as well as a terahertz measuring apparatus according to another aspect of the invention. Preferred further developments are described below.

Hereby, according to the invention, the terahertz measuring apparatus is provided, in particular, for carrying out the method according to the invention, and the method according to the invention is carried out, in particular, using or utilizing the terahertz measuring apparatus according to the invention.

Thus, a measuring apparatus having at least one terahertz transmission and reception unit the optical axis of which is adjustable and is adjusted during the measuring of the measurement object.

Hereby, according to one embodiment, the measurement object may be sensed by means of an additional sensor which detects the surface of the measurement object—contact-free or with contact—whereby the sensor signal of the sensors is received by a controller device and used for adjusting the optical axis of the transmission and reception unit.

Alternatively, according to a preferred embodiment, the optical axis of the transmitted terahertz radiation is adjusted continuously or periodically respectively about an adjustment range, and a measurement is carried out in various adjustment positions of the adjustment range. The adjustment may be carried out, in particular by pivoting or rotating respectively so that the optical axis is adjusted by an adjustment angle and a measurement is carried out in various angular positions of the adjustment angle. Moreover, translational adjustments are possible also. Following the measurements the amplitudes of the several measurements, which have been carried out within the adjustment range, are compared and the measurement having the highest amplitude of received terahertz radiation is used as the best measurement or, respectively, the measurement having an incidence angle closest to being perpendicular incidence. This measurement may directly be used as the measurement of the measuring method or used to adjust the optical axis.

Thus, with such a continuous adjustment of the optical axis within an adjustment range, e.g. adjustment angle, several advantages are attained:

Measurements with exactly or essentially perpendicular incidence of the terahertz radiation, leading to a high signal and exact measurements, can be carried out with little effort.

Hereby, no adjustment or tracking of the measurement object itself is required which may require high technical effort with some plastics products, in particular, directly after production where soft materials are involved. Thus, according to the invention, in particular, a continuous plastics products or one manufactured in an endless procedure, such as e.g. a plastic pipe or a plastic sheet, may be measured directly after the continuous production by means of the measuring apparatus.

Moreover, using periodic adjustment of the optical axis within an adjustment range a continuous adjustment procedure can be attained without, for example, having to adjust the measuring head specifically to a determined mal-adjustment each time; the subsequent determination of which measurement exhibits the highest amplitude is sufficient so that this measurement can be used directly. Also, hereby, for example, no intermediate stops of the adjustment motor are required to take the individual measurements in different adjustment positions or measurement positions respectively;

rather, the measurements may be carried out during the periodical adjustment without any stop of the adjustment motor because the run-time of the terahertz radiation is very short and there is no relevant mechanical shift of the optical axis within one measurement.

The adjustment of the optical axis may be carried out in accordance with differing embodiments:

Thus, for one thing, a measuring head with its optical axis may be adjusted in its entirety, for example, using an angular adjustment motor or e.g. a translational adjustment motor. Alternatively, the transmitter and the receiver of the terahertz radiation may remain fixed and the terahertz radiation may be adjusted via an optical array, for example, a mirror array comprising at least one adjustable mirror, for example, a metal mirror, prism or other reflective surface so that the mass to be adjusted is low. Thus, for example, an adjustable mirror in the beam path may be adjusted continuously by half of the adjustment angle. Hereby, for showing the optical axis of the terahertz beam, it is also possible to additionally include, for example, a laser beam in the visible range.

The adjustment can happen in a single axis or two axes. Where the adjustment happens only in one axis the adjustment can be carried out, in particular, perpendicular to the direction of transport, i.e. about an adjustment axis parallel to the direction of transport. Further, in addition to adjusting an axis, for example, the distance between a measuring head and the measurement object may be varied also. In the event of an adjustment about two axes e.g. the adjustment angles to the two axes or, respectively, the directions may differ, depending on the measurement object to be examined; thus, an adjustment angle perpendicular to the direction of transport direction of conveyance of the measurement object to be examined may be larger because, in this case, mal-adjustments or positioning errors, for example, tube positioning errors of a plastic pipe to be examined, may lead to larger angular errors than with a mal-positioning of the surface of the measurement object along the direction of transport.

In the event of a measuring apparatus comprising several terahertz transmitter/receiver devices arranged, for example, distributed around the direction of circumference, the measurement results or, respectively, the values determined from the measurements can also be compared to each other and used for the other terahertz transmitter/receiver devices. Thus, it is possible to use the run-time of the terahertz signal to also determine the distance between the surface and the transmission and reception unit or the measuring head thereof respectively and, from this in turn, for example, the position or deviation of the axis of symmetry of a plastic pipe from a center of axis of the measuring apparatus.

According to the invention, in particular, a layer thickness and/or a distance of the measurement object, e.g. also an outside dimensioning may be determined. The layer may be e.g. a wall of a measurement object, but also free space, e.g. the interior clearance of a tube as an air-filled layer.

The terahertz radiation may be utilized, in particular, in the frequency range between 0.01 THz and 50 THz, in particular, 0.05 THz and 20 THz. Hereby, the terahertz radiation can be transmitted and received, in particular, fully electronically by means of a transmitter/receiver dipole.

The measurements and evaluations can be carried out in the time domain or, alternatively, Fourier transformed in the frequency domain.

Figure 2:
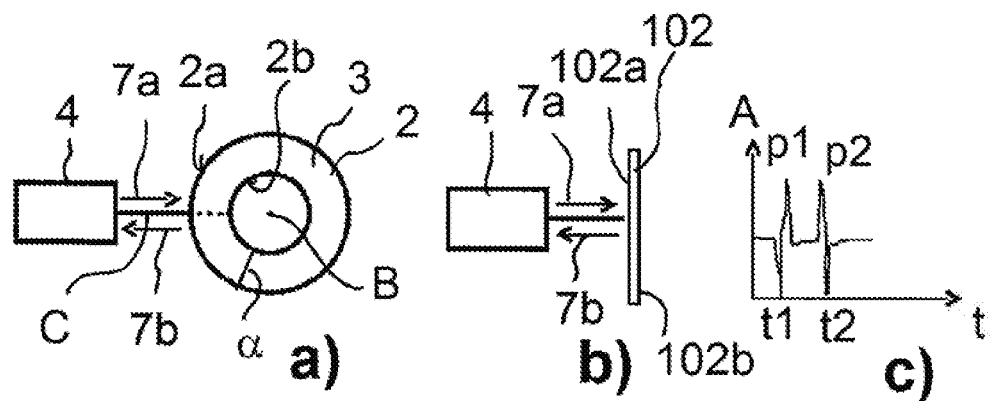
Figure 3:
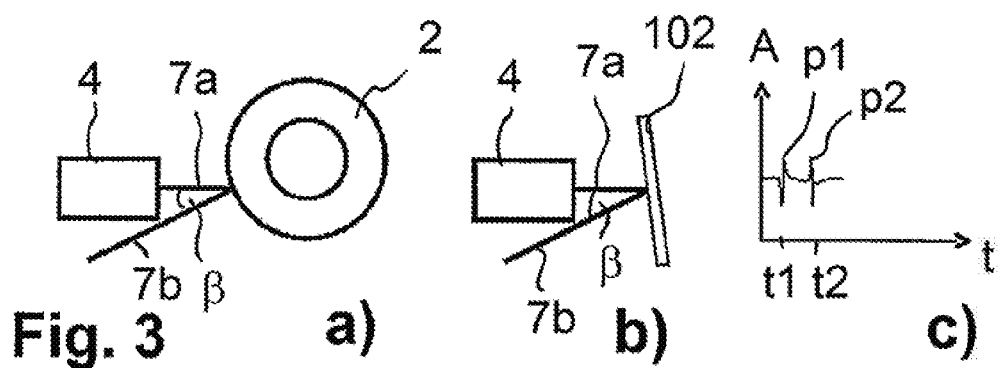
Figure 4:
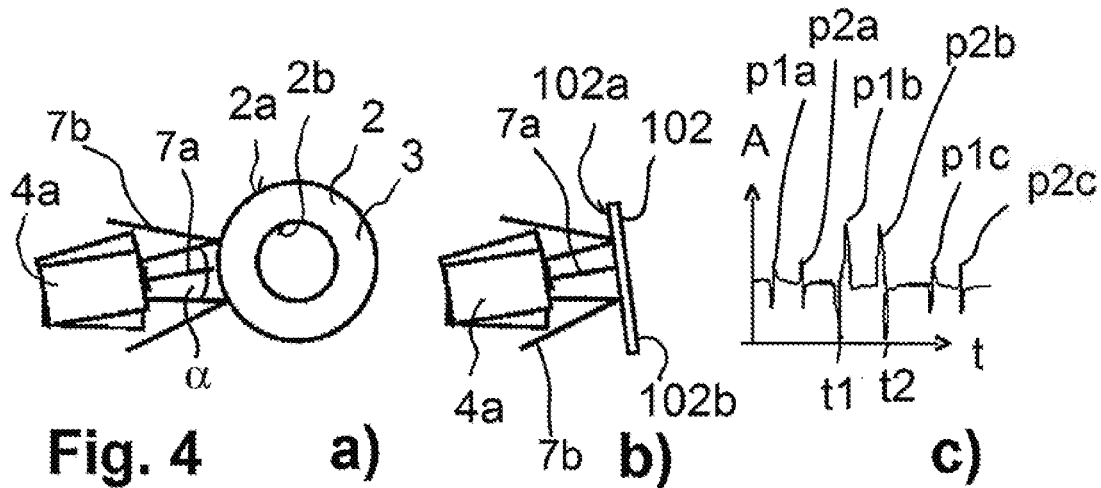
Figure 5:
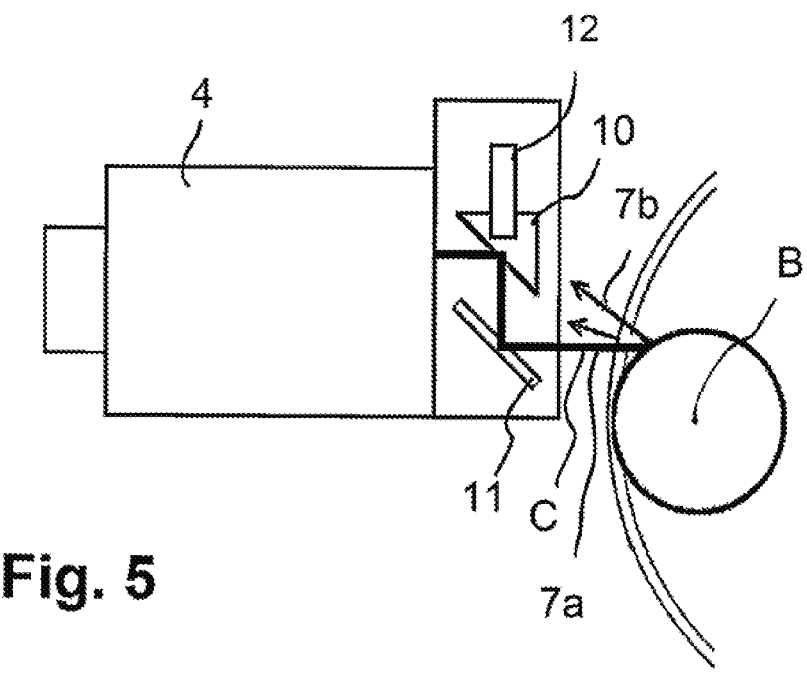
Figure 6:
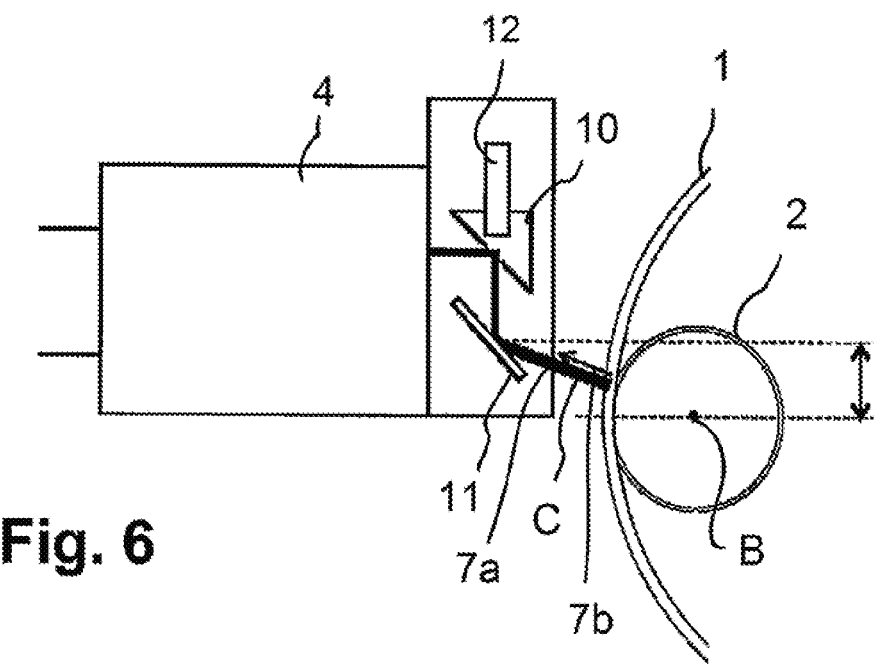
Figure 11:
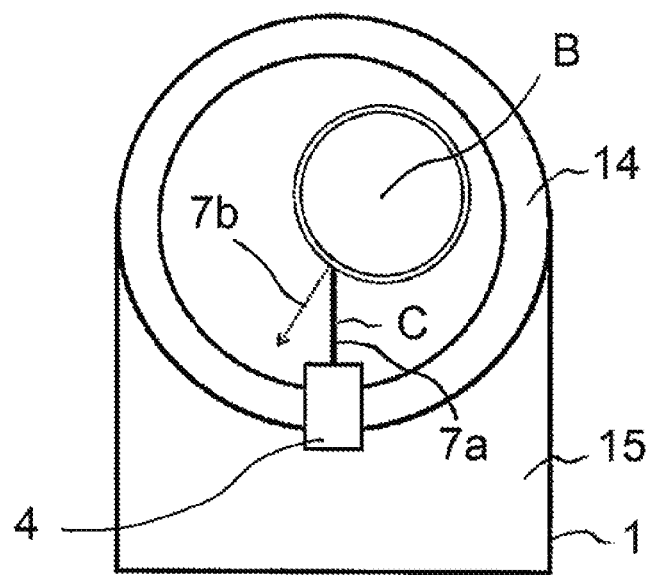
Figure 12:
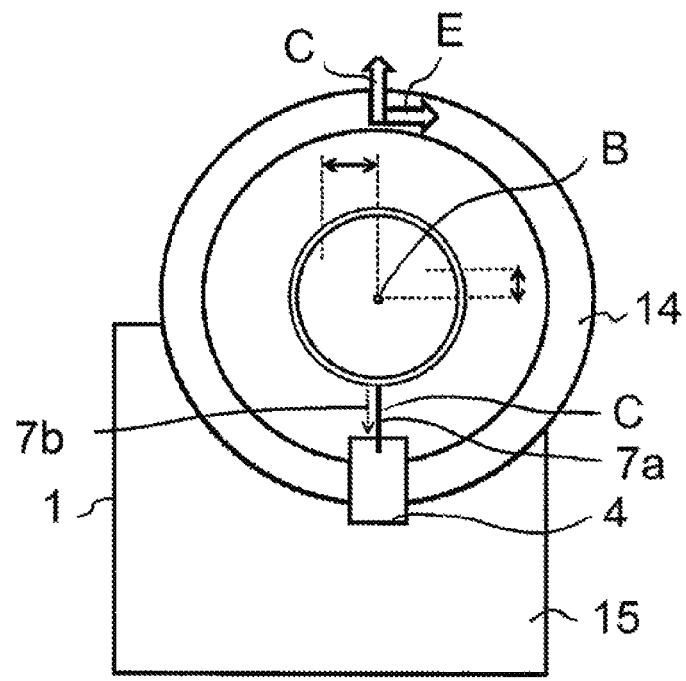

A few embodiments of the invention are subsequently illustrated by means of the attached drawings. These show in:

FIG. 1 a section through a measuring apparatus for measuring a measurement object in the form of a tube in the event of imprecise centering without or, respectively prior to, adaptation of the angular position;

FIGS. 2a, 2b, and 2c the measuring principle of determining a layer thickness or wall thickness of a measurement object made of plastics when applying a terahertz wall thickness measurement with optimum centering of the measuring apparatus;

FIGS. 3a, 3b, and 3c the measuring principle from FIGS. 2a, 2b, and 2c with imprecise centering of the measuring apparatus;

FIGS. 4a, 4b, and 4c the measuring situation with the method for the measuring a layer thickness according to an embodiment of the invention;

FIG. 5 an embodiment of a measuring apparatus with imprecise angular adjustment; and FIG. 6 the embodiment corresponding to that of FIG. 5 with subsequent compensation by means of angular adjustment of the measuring apparatus;

FIGS. 7, 8 an embodiment with translational adjustment of a mirror array;

FIGS. 9, 10 an embodiment with translational adjustment of a measuring head of the terahertz measuring apparatus; and FIGS. 11, 12 an embodiment with translational adjustment of a support ring of the measuring apparatus.

A terahertz measuring apparatus 1 serves for measuring a measurement object 2, in this case a plastic pipe 2, having a cylindrical or tube-shaped wall 3 having a wall thickness d. The measuring apparatus 1 may be provided, in particular, directly in line at the end of the manufacturing process, for example an extruder, and, correspondingly, the plastic pipe 2 is guided through the terahertz measuring apparatus 1 in the longitudinal direction, i.e. the direction of production and direction of conveyance.

Ideally, the plastic pipe 2 is guided axially or centrically, i.e. having its tube axis B on the symmetry axis A of the terahertz measuring apparatus 1; however, in accordance with FIG. 1, there may be a de-centered position, i.e. a pipe positioning error where the tube axis B deviates from the symmetry axis A. Such positioning error may appear during a sagging of the plastic pipe 2 or, respectively, due to vibrations of the resilient material of the freshly extruded plastic pipe 2.

The terahertz measuring apparatus 1 comprises several terahertz transmission and reception units 4 distributed across the circumference of the terahertz measuring apparatus 1 and aligned towards the interior, according to FIG. 1 towards the symmetry axis A.

The terahertz transmission and reception units 4 each comprise a terahertz transmitter, indicated in FIG. 1, for transmitting terahertz radiation 7a, in particular, in the frequency range between 0.01 THz and 50 THz, in particular, 0.05 THz and 20 THz, and in particular 0.1 THz and 10 THz, as well as an, indicated, receiver device 6 for receiving backwards reflected terahertz radiation 7b in the aforementioned frequency range. The determination happens in a controller unit 8 whereby each of the terahertz transmission and reception units 4 may have its own controller unit 8 or a common controller unit 8 is provided for the several terahertz transmission and reception units 4. The FIGS. 2*a* through 4*c* show the measuring principle in more detail:

FIGS. 2*a*, 2*b*, and 2*c* show measurements in correct alignment. According to FIG. 2*a* the transmission and reception unit 4 terahertz emits radiation 7*a* centrally onto the plastic pipe 2; according to FIG. 2*b*, correspondingly, terahertz radiation 7*a* is radiated vertically onto a plastic sheet 102 serving as measurement object. The plastics material of the two measurement objects 2 and 102 is respectively transparent for the terahertz radiation 7; however, while vacuum or air exhibit a refraction index of n=1 the plastics material has a refraction index of about 1.5. Thus, on the boundary surface transitions, i.e. on the outside of the tube wall 2*a* and the inside of the tube wall 2*b* or, respectively, der the outside of the sheet 102*a* and the inside of the sheet 102*b*, there will each be a partial reflection of the terahertz radiation 7. FIG. 2*c* shows the measuring diagram of the amplitude A of the received terahertz radiation, where the measurement peak p1 can be seen at time t1 and the measurement peak p2 at time t2, the time difference between t2−t1 representing the propagation time difference of the terahertz radiation 7 upon twice running through the pipe wall 3 with the wall thickness d and the refraction index n, i.e. e.g.

$$d=c(t2-t1)/2n$$

In the event of the imprecise centering according to FIGS. 3*a*, 3*b*, and 3*c* which, consequently, exists with most of the terahertz transmission and reception units 4 of FIG. 1, the optical axis C of the terahertz transmission and reception unit 4 according to FIG. 3*a* does not run through the tube axis B of the plastic pipe 2 or, according to FIG. 3*b*, not perpendicular to the plastic sheet 102 so that the reflected terahertz beam 7*b* is not reflected backwards exactly in the optical axis C but, rather, is reflected backwards in an error position angle β≠0 in shifted relation to the optical axis C. Thus, according to FIG. 3*c* a weak amplitude of the measurement signal is apparent which may even vanish entirely in the event of a large error position angle. Besides a weaker signal, errors in the measurement may ensue.

According to the invention, the angular position or, respectively, a mal-adjustment of the optical axis C of the terahertz transmission and reception unit 4 in relation to the surface 2*a* or 102*a* is determined and corrected, or a perpendicular measurement is determined by means of measurements and comparison with different angular positions.

Hereby, differing embodiments are provided by means of which a measurement with perpendicular alignment of the optical axis is attained.

According to a first alternative A, the surface 2*a* or 102*a* is covered by a further sensor serving as position sensor. The position sensor may contactlessly or with contact detect the exact position of the measurement object 2 or 102 so that the measuring head 4*a*, and thereby the positions of the optical axis C, is automatically adjusted correspondingly and aligned perpendicular onto the surface 2*a* or 102*a*.

According to alternative B, several measurements are carried out within an adjustment angle range α, and the proper position, i.e. a perpendicular incidence of the optical axis C to the measured surface 2*a* or 102*a*, is determined from the measurements. Hereby, too, several embodiments are possible:

In FIGS. 4*a* and 4*b*, a measuring head 4*a* is motor adjustable in its angular position in one or two axes so that the optical axis C of the measuring head 4*a* is adjusted in one or two directions. Hereby, in addition to adjusting one axis, it is also possible to vary a distance d4 from the measuring head 4*a* to the test object 2 or 102.

Thus, according to the embodiment of FIGS. 4*a*, 4*b*, and 4*c*, the measuring head 4*a* of each terahertz transmission and reception unit 4 can be adjusted separately by adjustment about an axis with an adjustment angle range α while measuring the signals according to FIG. 4*c*, whereby in the continuous measurements an optimum angular position is present with the peaks of the highest intensity I, thus, according to FIG. 4*c*, the peaks p1b, p2b, i.e. with the second of the three measurements. Thus, upon scanning this axis in the second measurement showing the peaks p1b, p2b, the optimum angular position or, respectively, the perpendicular angular position is reached and subsequently passed. In general, the optimum alignment in relation to the measurement object 2 or 102 is reached or sufficiently exactly reached respectively in a complete picoting procedure or scan of the adjustment angle range α so that no further measurement is required thereafter and the measurements with maximum amplitude may be used directly.

This scan by changing the angular position, i.e. adjusting the optical axis C with the adjustment angle range α, may be carried out e.g. in two axes successively.

The position of incidence of the terahertz radiation 7, i.e. the point of intersection of the optical axis C with the surface 2*a* or 102*a*, may also be calculated and determined by means of the measured angular or translation position of the adjustment of the position sensor or the adjustment of the terahertz radiation 7 or the optical axis C respectively, in combination with the terahertz propagation time signal.

Thus, for example, in the array according to FIG. 1, a run time measurement through a terahertz transmission and reception unit 4 may also serve, in addition to adjusting this terahertz transmission and reception unit 4 or, respectively, its optionally also adjustable measuring head 4*a*, to determine, by means of a propagation time measurement, the distance of the measurement object 2 to the terahertz transmission and reception unit 4 so that the absolute position is known so that the aberrant positioning of the tube axis B in relation to the symmetry axis A of the measuring apparatus 1 can be determined and, based on this, it is also possible to align or correct also the other terahertz transmission and reception units 4. Thus, in the embodiment according to FIG. 1 with a terahertz measuring apparatus 1 with several terahertz transmission and reception units 4 arranged in the direction of the circumference it is unnecessary for all terahertz transmission and reception units 4 to carry out such a compensation of the angular position or a determination of the mal-position in order to carry out a compensation or correction of the position.

FIGS. 5 and 6 show a further embodiment where the compensation of the angular position of the optical axis C of the terahertz transmission and reception unit 4 is corrected whereby, in this case, it is not the measuring head 4*a* that is adjusted, but the terahertz beam 7 is deflected via one or more mirrors 10, 11, for example, a fixed mirror 10 and an adjustable mirror 11. By adjusting the adjustable mirror 11 the optical axis C can be adjusted accordingly so as to compensate the angular position. Thus, in this embodiment, an adjustment of the adjustable mirror by one half of the adjustment angle range α so that the optical axis C scans the adjustment angle range a in order to determine the optimum angular position, again with continuous measurements in accordance with the diagram of FIG. 4*c*, whereby the optimum measurement may be utilized immediately as the relevant measurement.

According to FIGS. 5 and 6, for example, the fixed mirror 10 is designed as a prism or semi-transparent mirror so that here—or at another point—an optical laser 12 can be superimposed on the terahertz beam 7 as position marker. The superimposition may serve for visual inspection, moreover, in principle, the measuring apparatus 1 may contain an optical camera for detecting the points generated by the position marker and determining the position of the measurement object 2, 102.

Thus, according to the invention, it is possible to continuously correct an angular position of all terahertz transmission and reception units 4 in-line during production of the measurement object, for example the plastic pipe 2 or the plastic sheet 102 shown in FIG. 1.

Besides such angular adjustments, translational adjustments of the optical axis C of the emitted terahertz radiation 7a are still possible. The FIGS. 7 through 12 show various embodiments of such translational adjustments:

According to FIG. 7 and FIG. 8, the adjustable mirror 11 is not pivoted but adjusted translationally. Thus, the mirror surfaces of the fixed mirror and the adjustable mirror 11 extend e.g. always parallel to each other. Thus, the adjustable mirror 11 is e.g. translationally adjusted from the starting position according to FIG. 7 and reaches in the position of FIG. 8 the measuring position, where the emitted terahertz radiation 7a hits the wall of the measurement object 2 perpendicularly, which in turn is determined as the maximum amplitude or maximum detected signal. Thus, again, several measuring positions of the adjustable mirror 11 are reached in which measurements are carried out. In the shown embodiment according to FIGS. 7 and 8 the fixed mirror 10 re-directs the emitted terahertz radiation 7a by a right angle; with such an embodiment it is also sensible to adjust the adjustable mirror 11 in this direction of adjustment E, running perpendicular to the optical axis C and also perpendicular to the tube axis B of the measurement object 2, whereby, however, other translational adjustment directions are possible. According to FIG. 8, e.g. an adjustment range s of the adjustable mirror 11 is set until a measuring position with perpendicular incidence of the terahertz radiation 7a onto the measurement object 2 is reached. The further illustrations relating to the afore-mentioned embodiments apply similarly to the embodiment of FIGS. 7, 8.

According to the embodiment of FIGS. 9 and 10 not only an adjustable mirror 11 of a mirror array but the entire measuring head 4a is adjusted translationally along a guide device 17, e.g. again in an adjustment direction E perpendicular to the optical axis C and perpendicular to the tube axis B or symmetry axis of the respective measurement object 2, so that again measurements can be taken in the different adjustment positions or measuring positions and compared to each other, with a corresponding evaluation of the measurements according to the embodiments described above so that, according to FIG. 10, in the event of an adjustment distance s a perpendicular incidence of the terahertz radiation is attained.

In the embodiment of FIGS. 11 and 12 not only a single measuring head 4a but the entire measuring apparatus 1 or a support ring 14, on which the terahertz transmission and reception units 4 are arranged in ring shape, is translationally adjusted against e.g. a frame 15 or base 15 of the terahertz measuring apparatus 1. Hereby, e.g. adjustments in two axes or the plane perpendicular to the tube axis B and to the symmetry axis A of the measuring apparatus 1 can be carried out, i.e. e.g. as drawn in the adjustment direction E and an adjustment direction along the optical axis C, or another axis in this plane.

Moreover, any combinations of pivoting, i.e. adjustments about adjustment angles, and translational adjustments are possible.

The invention claimed is:

1. A method for measuring using terahertz radiation, comprising:
    (a) radiating at least one terahertz beam from a terahertz transmission and reception unit along an optical axis onto a measurement object;
    (b) detecting terahertz radiation passing through or reflected by at least one layer of the measurement object;
    (c) evaluating a measurement signal of the reflected terahertz radiation detected; and
    (d) ascertaining measurement value from a propagation time difference of the radiation reflected on at least one boundary surface of said at least one layer,
    wherein a plurality of measurements are carried out using different optical axes of the terahertz radiation emitted;
    wherein the optical axes are adjusted during or between the measurements;
    wherein the optical axis of the emitted terahertz radiation is adjusted at least periodically across an adjustment range, and multiple measurements are recorded during the adjustment;
    wherein said multiple measurements are compared to each other; and
    wherein a measurement having a maximum amplitude or a maximum detected signal is used as the measurement for ascertaining the measurement variable.

2. The method according to claim 1, wherein a surface of the measurement object is detected by a sensor and the optical axis of the emitted terahertz radiation is aligned and re-adjusted, depending on the measurement of the sensor, to a position of minimum distance as determined by said sensor.

3. The method according to claim 1, wherein the optical axis of the emitted terahertz radiation is adjusted periodically in two directions not parallel in relation to each other by adjustment ranges.

4. The method according to claim 2, wherein the optical axis of the emitted terahertz radiation is adjusted by pivoting a measuring head of the terahertz transmission and reception unit by the adjustment angle.

5. The method according to claim 2, wherein the terahertz transmission and reception unit comprises a mirror array comprising an adjustable mirror for deflecting the emitted and reflected terahertz radiation, said adjustable mirror being adjusted for changing the optical axis.

6. The method according to claim 1, wherein a position of incidence of the emitted terahertz radiation onto the surface of said measurement object is determined and identified from the measurement, in particular, a determination of the propagation time.

7. The method according to claim 1, wherein the optical axis of the emitted terahertz radiation is adjusted during the measurements or between the measurements translationally.

8. The method according to claim 1, further comprising:
    guiding a plastics product generated in a manufacturing device, after having been manufactured, continuously in a direction of transport along a measuring apparatus having at least one terahertz transmission and reception unit; and
    examining the plastics product using said terahertz transmission and reception unit for a layer thickness;

wherein the optical axis of the emitted terahertz radiation is aligned perpendicular to the direction of transport and is adjusted in a plane perpendicular to the direction of transport; and wherein the layer thickness is determined by a propagation time measurement in which a temporal difference between a first measurement peak of the reflection upon entry of the terahertz radiation into a surface of the layer and a second measurement peak (p2), later in time, following transmission of the layer and reflection upon exit from said layer is determined, the layer thickness d being ascertained from d=c(t2−t1)/2n, where c is the speed of light in a vacuum, n is the refraction index of the plastics material for the terahertz radiation and is the time difference between the first measurement peak and the second measurement peak.

9. A terahertz measuring apparatus comprising
a terahertz transmission and reception unit with a transmitter for emitting terahertz radiation along an optical axis onto a measurement object,
a receiver for receiving the terahertz radiation, reflected from said measurement object, and
a controller unit for ascertaining a measurement value from a propagation time difference of the terahertz radiation reflected on a first boundary surface or outer surface of the layer and the terahertz radiation reflected after passage through said layer on a second boundary surface,
wherein at least one part of said terahertz transmission and reception unit is adjustable for adjusting the optical axis about an adjustment range and said controller unit is configured to determine the measurement variable from a comparison of several measurements at different adjustments of the optical axis.

10. The terahertz measuring apparatus according to claim 9, wherein a measuring head of said terahertz measuring apparatus is adjustable in at least one pivot axis about the adjustment angle.

11. The terahertz measuring apparatus according to claim 9, further comprising a mirror array having at least one adjustable mirror adjustable about at least an adjustment range for adjusting the optical axis of the emitted terahertz radiation.

12. The terahertz measuring apparatus according to claim 9, further comprising a sensor for detecting a position and/or location of a surface of said measurement object and said controller unit tracks the optical axis depending on the location detected by said sensor.

13. The terahertz measuring apparatus according to claim 9, wherein said controller unit adjusts the optical axis periodically within an adjustment range, and continuously records measurement signals in said adjustment range, said controller unit utilizing a measurement with maximum amplitude as the measurement with perpendicular incidence onto a surface of said measurement object.

14. A method for measuring using terahertz radiation, the method comprising:
(a) radiating at least one terahertz beam from a terahertz transmission and reception unit along an optical axis onto a measurement object;
(b) detecting terahertz radiation passing through or reflected by at least one layer of the measurement object;
(c) evaluating a measurement signal of the reflected terahertz radiation detected; and
(d) ascertaining a measurement value from a propagation time difference of the radiation reflected on at least one boundary surface of said at least one layer,
wherein a plurality of measurements are carried out using different optical axes of the terahertz radiation emitted;
wherein the optical axes are adjusted during or between the measurements;
wherein a surface of the measurement object is detected by a sensor and the optical axis of the emitted terahertz radiation is aligned and re-adjusted, depending on the measurement of the sensor, to a position of minimum distance as determined by said sensor;
wherein the optical axis is adjusted periodically in a direction by the adjustment angle; and
wherein a distance of a measuring head emitting the terahertz radiation to the measurement object is adjusted periodically.

* * * * *

UNITED STATES PATENT AND TRADEMARK OFFICE
CERTIFICATE OF CORRECTION

| | |
|---|---|
| PATENT NO. | : 10,584,957 B2 |
| APPLICATION NO. | : 16/062662 |
| DATED | : March 10, 2020 |
| INVENTOR(S) | : Thiel et al. |

Page 1 of 1

It is certified that error appears in the above-identified patent and that said Letters Patent is hereby corrected as shown below:

In Column 8, Line 17 after "ascertaining" please add --a--.
    In Column 9, Line 9 (Line 17 of Claim 8) after "peak" please delete "(p2)".
    In Column 9, Line 15 (Line 23 of Claim 8) after "and" please add --(t2-t1)--.

Signed and Sealed this
Fifth Day of May, 2020

Andrei Iancu
*Director of the United States Patent and Trademark Office*